(12) United States Patent
Moharir et al.

(10) Patent No.: US 10,423,760 B2
(45) Date of Patent: *Sep. 24, 2019

(54) METHODS, SYSTEM AND APPARATUS FOR TRANSCRIBING INFORMATION USING WEARABLE TECHNOLOGY

(71) Applicants: Vik Moharir, San Jose, CA (US); Mike Lee, Belmont, CA (US); Bidyut Parruck, Cupertino, CA (US)

(72) Inventors: Vik Moharir, San Jose, CA (US); Mike Lee, Belmont, CA (US); Bidyut Parruck, Cupertino, CA (US)

( * ) Notice: Subject to any disclaimer, the term of this patent is extended or adjusted under 35 U.S.C. 154(b) by 228 days.

This patent is subject to a terminal disclaimer.

(21) Appl. No.: 15/456,763

(22) Filed: Mar. 13, 2017

(65) Prior Publication Data

US 2017/0185738 A1 Jun. 29, 2017

Related U.S. Application Data

(63) Continuation-in-part of application No. 15/381,935, filed on Dec. 16, 2016, which is a
(Continued)

(51) Int. Cl.
*H04N 5/77* (2006.01)
*G06F 19/00* (2018.01)
*G06Q 50/24* (2012.01)
*G10L 15/26* (2006.01)
*H04N 5/225* (2006.01)
*H04N 7/14* (2006.01)
*H04N 7/18* (2006.01)
(Continued)

(52) U.S. Cl.
CPC .......... *G06F 19/3418* (2013.01); *G02C 11/10* (2013.01); *G06Q 10/10* (2013.01); *G06Q 50/24* (2013.01); *G10L 15/265* (2013.01); *G16H 10/60* (2018.01); *G16H 40/67* (2018.01); *G16H 80/00* (2018.01); *H04N 5/2252* (2013.01); *H04N 5/2257* (2013.01); *H04N 5/77* (2013.01); *H04N 7/142* (2013.01); *H04N 7/147* (2013.01); *H04N 7/148* (2013.01); *H04N 7/185* (2013.01); *H04N 9/8042* (2013.01); *G06Q 50/22* (2013.01); *G10L 19/00* (2013.01); *H04N 2007/145* (2013.01); *H04R 1/028* (2013.01); *H04R 2430/01* (2013.01); *H04R 2499/11* (2013.01)

(58) Field of Classification Search
CPC ........ H04N 7/142; H04N 7/147; H04N 7/148; H04N 9/8042; H04N 7/185; H04N 5/2252; H04N 5/77; G16H 40/67; G16H 80/00; G16H 10/60; G02C 11/10; H04R 2430/01; H04R 2499/11
USPC ............................................ 348/14.01–14.16
See application file for complete search history.

(56) References Cited

U.S. PATENT DOCUMENTS 6,349,001 B1 * 2/2002 Spitzer .................... G06F 19/00
359/618
9,344,686 B2   5/2016 Moharir
(Continued)

*Primary Examiner* — Melur Ramakrishnaiah
(74) *Attorney, Agent, or Firm* — Haverstock & Owens LLP

(57) ABSTRACT

A wearable scribing system includes a camera and a microphone which communicate information to a remote system via a receiver/transmitter device. A scribe at the remote system inputs the information into an electronic health record. The wearable scribing system enables direct physician to physician communication.

20 Claims, 11 Drawing Sheets

Related U.S. Application Data continuation-in-part of application No. 15/013,979, filed on Feb. 2, 2016, now Pat. No. 9,524,530, which is a continuation-in-part of application No. 14/698,970, filed on Apr. 29, 2015, now Pat. No. 9,344,686.

(60) Provisional application No. 61/986,056, filed on Apr. 29, 2014.

(51) Int. Cl.

| | | |
|---|---|---|
| *G02C 11/00* | (2006.01) | |
| *H04N 9/804* | (2006.01) | |
| *G06Q 10/10* | (2012.01) | |
| *G16H 80/00* | (2018.01) | |
| *G16H 10/60* | (2018.01) | |
| *G16H 40/67* | (2018.01) | |
| *G06Q 50/22* | (2018.01) | |
| *G10L 19/00* | (2013.01) | |
| *H04R 1/02* | (2006.01) | |

(56) References Cited

U.S. PATENT DOCUMENTS

| | | | |
|---|---|---|---|
| 9,524,530 B2 | 12/2016 | Moharir | |
| 2003/0068057 A1* | 4/2003 | Miller | H04B 1/385 381/334 |
| 2003/0104806 A1 | 6/2003 | Ruef | |
| 2005/0066001 A1* | 3/2005 | Benco | H04L 29/06 709/204 |
| 2007/0273751 A1 | 11/2007 | Sachau | |
| 2009/0279884 A1* | 11/2009 | Matsumoto | G03B 17/02 396/448 |
| 2010/0277563 A1 | 11/2010 | Gupta | |
| 2011/0125533 A1* | 5/2011 | Budacki | G16H 10/60 705/3 |
| 2011/0173537 A1* | 7/2011 | Hemphill | G06F 17/30038 715/716 |
| 2012/0020577 A1* | 1/2012 | Yasrebi | H04L 51/34 382/229 |
| 2012/0068914 A1* | 3/2012 | Jacobsen | G06F 1/163 345/8 |
| 2012/0134661 A1 | 5/2012 | Ozaki | |
| 2012/0265529 A1* | 10/2012 | Nachtrab | G06F 17/289 704/235 |
| 2012/0317202 A1* | 12/2012 | Lewis | G01S 19/17 709/204 |
| 2013/0044128 A1* | 2/2013 | Liu | G09G 5/00 345/633 |
| 2014/0222462 A1 | 8/2014 | Shakil et al. | |
| 2014/0248838 A1 | 9/2014 | Hazell et al. | |
| 2014/0354758 A1 | 12/2014 | Spence | |
| 2015/0127340 A1 | 5/2015 | Epshteyn et al. | |
| 2015/0215753 A1 | 7/2015 | Leipzig et al. | |

* cited by examiner

METHODS, SYSTEM AND APPARATUS FOR TRANSCRIBING INFORMATION USING WEARABLE TECHNOLOGY

CROSS-REFERENCE TO RELATED APPLICATION(S)

This application is a continuation-in-part application of co-pending U.S. patent application Ser. No. 15/381,935, filed Dec. 16, 2016, and titled "METHOD, SYSTEM AND APPARATUS FOR TRANSCRIBING INFORMATION USING WEARABLE TECHNOLOGY," which is a continuation-in-part application of co-pending U.S. patent application Ser. No. 15/013,979, filed Feb. 2, 2016, and titled "METHOD, SYSTEM AND APPARATUS FOR TRANSCRIBING INFORMATION USING WEARABLE TECHNOLOGY," which is a continuation-in-part application of U.S. patent application Ser. No. 14/698,970, filed Apr. 29, 2015, and titled "METHOD, SYSTEM AND APPARATUS FOR TRANSCRIBING INFORMATION USING WEARABLE TECHNOLOGY," which claims priority under 35 U.S.C. § 119(e) of the U.S. Provisional Patent Application Ser. No. 61/986,056, filed Apr. 29, 2014 and titled, "SCRIBELINK," which are both hereby incorporated by reference in their entireties for all purposes.

FIELD OF THE INVENTION

The present invention relates to the field of the electronic health records. More specifically, the present invention relates to generating electronic health records using wearable technology.

BACKGROUND OF THE INVENTION

An Electronic Health Record (EHR) offers advantages over paper-based charts. However, EHRs suffer from a major drawback. The time required by physicians to enter information into the computer causes inefficiency and distracts attention away from the patient.

SUMMARY OF THE INVENTION

A wearable scribing system includes a camera and a microphone which communicate information to a remote system via a receiver/transmitter device. A scribe at the remote system inputs the information into an electronic health record. The wearable scribing system enables direct physician to physician communication.

DETAILED DESCRIPTION OF THE PREFERRED EMBODIMENT

Figure 1:
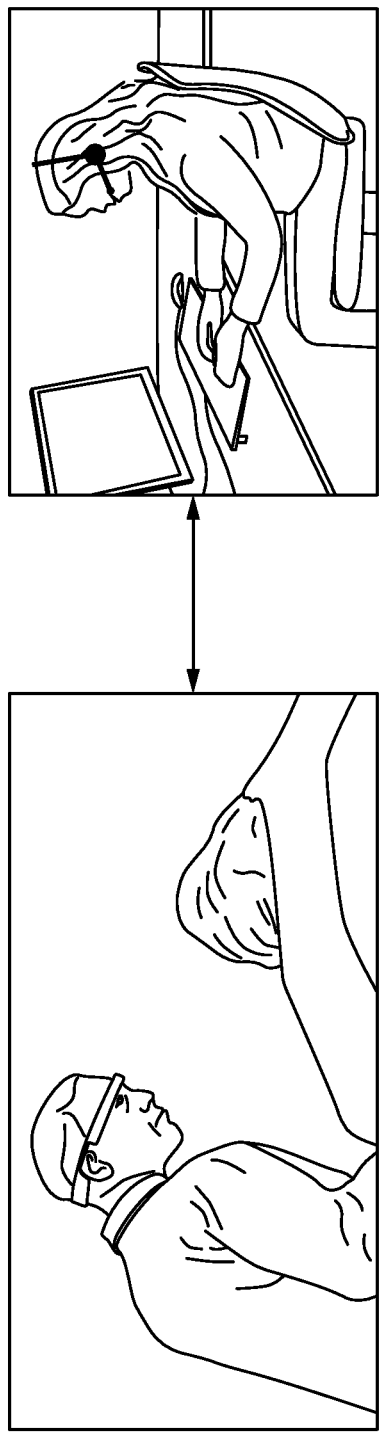
FIG. 1 illustrates images of a wearable scribing system according to some embodiments.

To overcome the problem of a doctor having to input information into a computer, a physician with smart glasses or another wearable communication device (e.g., Atheer Labs smart glasses, Google Glass®) has a real time connection to a scribe in a remote location as shown in FIG. 1. The physician wears a wearable scribing system which is able to acquire video and audio (e.g., using a video camera and a microphone) and a receiver/transmitter unit. The audio and video are transmitted to a scribe in a remote location (e.g., India) who enters the information into the electronic health record. In some embodiments, the scribe is able to communicate via audio and video with the physician.

The wearable scribing system includes an interface between a physician and a scribe. The physician has a wearable device (e.g., smart glasses with a video camera), an external microphone affixed to the smart glasses and a processing unit. In some embodiments, the processing unit is a device configured specifically for receiving and transmitting audio and video. In some embodiments, a waist pack contains a tablet computer/smart phone and an external battery pack, and these together serve as the processing unit. The smart glasses or wearable device interfaces with the receiver/transmitter via a wired connection or a wireless connection, such as Bluetooth®. The external microphone plugs into the headphone jack of the receiver/transmitter unit or communicates with the receiver/transmitter wirelessly. The receiver/transmitter relays the signals to the scribe via the Internet. In some embodiments, a single touch of an icon on the wearable device establishes the link between physician and scribe. In some embodiments, the link between the physician and scribe begins automatically upon startup of the wearable device and/or the receiver/transmitter or based on a voice command. In some embodiments, a server is used for buffering in between the receiver/transmitter and the scribe desktop computer. The receiver/transmitter is able to be worn anywhere (e.g., arm, wrist, leg). In some embodiments, the receiver/transmitter is not worn by the physician; rather, it is located in the room proximate to the wearable camera device.

The scribe documents into an EHR in real time as the physician performs a history and physical exam, discusses assessment and a plan with the patient, and in some instances verbalizes orders. The physician may elect to turn off the video feed but continue audio connection during the physical exam or vice versa, or turn off both.

The physician electronically signs orders on the wearable device or a computer of their choice. At the end of the visit, the scribe assigns billing and procedure codes to the encounter. The physician reviews the transcribed notes and billing codes and electronically signs the encounter as complete. This is able to be completed using the wearable scribing system or another computer. For example, the information input by the scribe is displayed on the display of the wearable scribing system, and the physician is able to use a voice command or a touch implementation on the wearable scribing system to electronically sign and/or make changes. The scribe marks the encounter as ready for billing.

Figure 2:
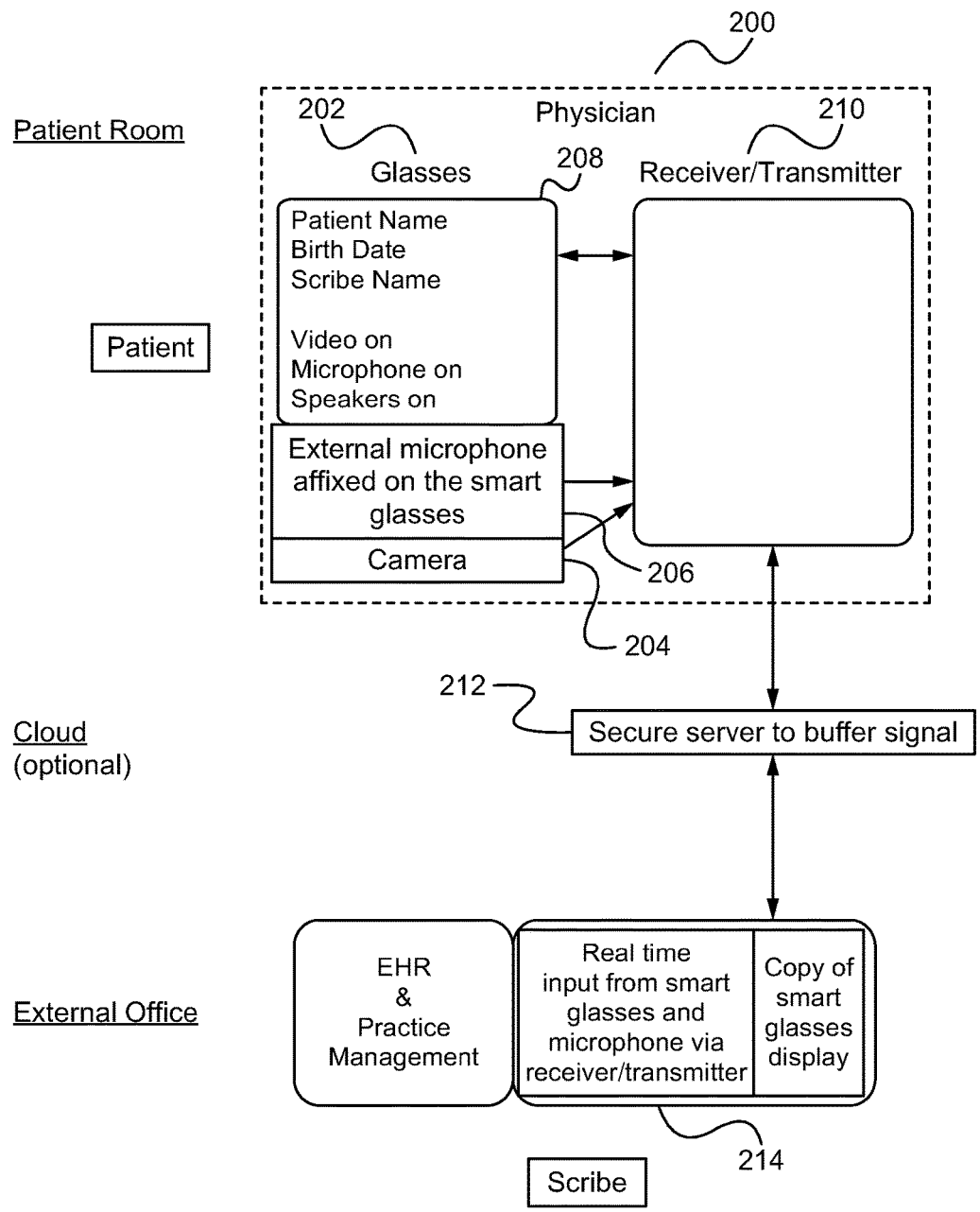
FIG. 2 illustrates a diagram of a wearable scribing system according to some embodiments.

FIG. 2 illustrates a diagram of the wearable scribing system according to some embodiments. In the patient room (or other clinical setting), a physician evaluates and treats a patient in the appropriate location: exam room, emergency department, procedure or operating room. The physician has a wearable scribing system 200. In some embodiments, the wearable scribing system 200 includes glasses 202 with a camera 204, a microphone 206 and a display 208 which communicate with a receiver/transmitter 210 (e.g., waist pack). In some embodiments, fewer or additional hardware is included such as a dedicated processor and/or additional circuitry. In some embodiments, the camera 204, the microphone 206 and/or the display 208 are attachable/detachable. In some embodiments, the glasses 202 are tethered to the receiver/transmitter 210 (e.g., the camera 204 and microphone 206 are wired to the receiver/transmitter 210), and in some embodiments, the glasses 202 communicate wirelessly to the receiver/transmitter 210. The receiver/transmitter 210 transmits and receives information via Wi-Fi and/or using any other network (e.g., cellular). For example, the receiver/transmitter 210 receives information from the camera 204 and microphone 206 and transmits that information to a server 212 in the cloud and/or to an external device 214 utilized by a scribe to receive/input the medical information (e.g., computer and headset).

The display 208 on the smart glasses wearable by the physician is able to display any of the following: patient name, patient birth date, indication whether the video output is on, indication whether the audio output is on, a live image of the scribe transmitted from the desktop camera of the scribe. This way the physician can be certain the scribe is interfaced. In some embodiments, the receiver/transmitter 210 includes a display, which, for example, is able to have any of the following icons: scribe link/unlink, video output on/off, video input on/off, audio output on/off and audio input on/off. In some embodiments, a full patient note is available for physician review on the smart glasses display for physician review and signature using the smart glasses. In some embodiments, the physician may access the full patient electronic health record and medical images using the smart glasses. In some embodiments, the smart glasses may be used for direct medical professional communications such as physician to physician or nurse to physician for the purposes of patient care. For example, captured content is able to be transmitted or shared between devices such as between professionals' computers or smart glasses. In some embodiments, the glasses 202 have touch sensors or buttons which toggle audio/video on/off, independently with a single touch.

In some embodiments, the cloud-based server 212 is used for a buffer in between the receiver/transmitter 210 and the device 214 of the scribe. This may allow for a smoother transmission but with the added cost of the cloud-based service.

At a remote location, a scribe has a device 214 (e.g., a desktop computer) and wears headphones with a microphone. In real time, the headphones put out the audio captured in the patient encounter. The scribe is able to use a microphone to communicate to the physician.

In some embodiments, a scribe computer screen displays the following: real time video from the smart glasses, a copy of the smart glasses display of the physician (so the scribe is aware of what the physician is viewing) and the electronic health record and practice management system with patient information. The scribe enters data in real time into software for physician review and signature.

In some embodiments, the wearable scribing system 200 includes smart glasses 202 (e.g., Atheer Labs smart glasses, Google Glass®), an external microphone 206 affixed to the smart glasses 202, and a waist pack. In some embodiments, the waist pack is solely composed of a dedicated receiver/transmitter unit. In some embodiments, the waist pack contains a tablet computer/smart phone as the receiver/transmitter 210 and an optional external battery pack. The smart glasses 202 interface to the receiver/transmitter unit or tablet via a wired or a wireless connection, such as Bluetooth®. The external microphone 206 plugs into the headphone jack of the receiver/transmitter unit or tablet/phone communicates wirelessly. The receiver/transmitter unit or tablet/phone transmits and receives information via Wi-Fi and/or using any other network (e.g., cellular).

In some embodiments, the wearable scribing system includes a setup process for small entities. A physician registers online and notifies a hosting company of the following: practice name and demographics, specialty, current EHR used, current Practice Management (PM) system used, current method of billing, do they wish for the host company to handle the PM system, smart glasses design request, requested start date, typical work schedule, the physician makes a credit card payment if they do not wish for the host company to handle PM, contract signed online, physician satisfaction survey-pre implementation, physician gives consent, with online signature, for the host company to have access to the EHR and PM of physician, the host company obtains access for scribes to document on the EHR and PM, the host company ensures that the EHR and PM has scribe functionality in that the scribe may enter notes and orders and indicate that they are ready for signature, the orders would not be official until reviewed and signed by a physician, the notes would not be official until reviewed and signed by a physician, work schedule created for scribes with extra 25% hours allocated to ensure continued coverage of physicians in case they exceed an anticipated schedule, physician schedule modified: training time blocked, day one of go live=50% volume, days two and three=66% volume, smart glasses, receiver/transmitter, batteries, charger, and cables sent to physician, link to online instruction for smart glasses fitting placed in package, practices notified on the importance of proper charging of batteries and having back up, instructions placed in package on checking for full Wi-Fi connectivity, one week prior to going live, physician performs and scribe make a test run with mock patient, and go live. In some embodiments, fewer or additional steps are implemented.

In some embodiments, the wearable scribing system includes a setup process for large entities. Organizations give names of all physicians, their specialty, typical schedule, and requested smart glasses style, organization name and demographics, current EHR used, current PM system used, current method of billing, do they wish for the host company to handle PM system, requested date to begin roll out and roll out schedule, organization makes credit card payment if they do not wish for the cost company to handle PM, contract signed online, physician satisfaction survey—pre implementation, organization gives consent, with online signature, for the host company to have access to the EHR and PM system, the host company obtains access for scribes to document on the EHR and PM, work schedule created for scribes with extra 25% hours allocated to ensure continued coverage of physicians in case they exceed anticipated schedule, physician schedule modified: training time blocked, day one of go live=50% volume, days two and three=66% volume, smart glasses, receiver/transmitter, batteries, charger, and cables sent to physician, link to online instruction for smart glasses fitting placed in package, practices notified on the importance of proper charging of batteries and having back up, instructions placed in package on checking for full Wi-Fi connectivity, one week prior to going live, physician performs and scribe make a test run with mock patient, go live as per roll out schedule, for large organizations, the host company provides a representative during roll out. In some embodiments, fewer or additional steps are implemented.

In some embodiments, the wearable scribing system includes a process for clinical use. The front desk registers the patient into the EHR, nurse places patient into a room (many clinics use medical assistants instead of nurses). Nurse takes the vital signs and obtains pertinent medical history (allergies, past medical history, safety screening) in the level of detail per facility protocol. Nurse enters the information into the EHR. The physician indicates to the scribe, who is based elsewhere (e.g., India), the patient they will see next or on whom they next wish to enter orders or dictate other documentation. The scribe, on their own desktop running the EHR software, opens the chart of the patient. All transmissions and aspects of the encounter and the host company adhere to HIPAA standards. A step in maintaining HIPAA compliance is to have the connectivity to the external system of the scribe as the only feature on the smart glasses. In some embodiments, all other applications such as email, recording, photos are disabled. A separate receiver/transmitter (e.g., tablet computer) that will provide wireless connectivity is provided. In some embodiments, the receiver/transmitter will also have all functions other than connectivity to the external system and EHR disabled. Prior to entering the room or once inside the patient room and after greeting the patient, the physician reviews the entered data as well as any necessary information from prior medical care. Unless specifically stated, the physician should perform all reviews on a device with which they feel most comfortable. Examples include: tablet computer, smart phone, and desktop. For efficiency, the device is located in the patient room or just outside the door. The device the physician uses for chart review should have rapid login capabilities with the scribing system automatically starting on login. The physician, wearing smart glasses, enters the room. The smart glasses will have clear lens so they can be used as part of the universal precautions against blood borne pathogens. The smart glasses have a HIPAA compliant secure video and voice link to the scribe. The image in the smart glasses display will have a live video of the scribe. This way the physician knows the scribe stands ready to document. The physician confirms identity of the patient by greeting them by name. For facilities that use wrist bands, the physician will look at the wrist band as well. The scribe will overlay the patient name, date of birth, and section being worked upon (history, orders, prescriptions, letter) on the smart glasses display. This permits the physician to know at all times the patient and section for which the scribe enters data. The physician obtains the patient history as usual and the scribe documents in real time. Prior to beginning the physical exam, the physician turns off the video feed originating from smart glasses but keeps on the audio as well as the smart glasses screen displaying the scribe and patient identification. "Video feed off" will appear in the display. During the physical exam, the physician will dictate as they examine and the scribe will continue to enter data— "HEENT exam is normal . . . the cardiac exam is normal . . . the lungs have faint wheezing in bilateral lower lobes . . . " Common sense is employed to maintain sensitivity. In the presence of the patient, the physician should not dictate items such as "the patient is a morbidly obese male appearing much older than stated age." The physician turns on the video feed to the scribe. The scribe continues to enter the note as physician performs subsequent steps. The physician discusses their assessment and treatment plan with the patient. The physician dictates orders for items such as medication, laboratory tests, and imaging. However, per The Joint Commission, these orders cannot be officially entered and carried out until reviewed and electronically signed by a physician [Joint Commission]. The physician reviews the orders entered by the scribe and electronically signs orders on a computer of their choice. If a patient, either the current one or one previously evaluated is not ready for discharge, the physician and scribe move onto next patient and repeat the steps above. As additional information becomes available, such as completed test results and recommendations from consulting physicians, the doctor and scribe ensure entry of these details into the EHR. If a patient is ready for discharge, the physician reviews the transcribed notes for accuracy. The scribe assigns a billing code to the visit and reviews with the physician to ensure they agree. If needed the physician can clarify the note to ensure the billing level matches the work performed. The physician signs the note as complete. The scribe immediately marks as ready for billing and submits for payment. After the patient visit, as additional information becomes available, such as follow up telephone conversations with the patient, completed test results, and recommendations from consulting physicians, the doctor and scribe ensure entry of these details into the EHR. The patient authorization to use the scribing system will be included in the general consent forms all patients sign, and the patient has the right to decline the use of the scribing system. In some embodiments, contingency plans are implemented. For example, a video recording of history and physical is directly stored in smart glasses with digital storage in the case of a connection loss to the scribe. The scribe will transcribe the encounter when the connection is reestablished or when the scribe is able to download the video file. In some embodiments where smart glasses are not available, the physician is able to dictate the encounter notes or the physician may also chose to type the note directly into the EHR. A paper and pen are able to be used in the case of full computer or electrical outage.

Figure 3:
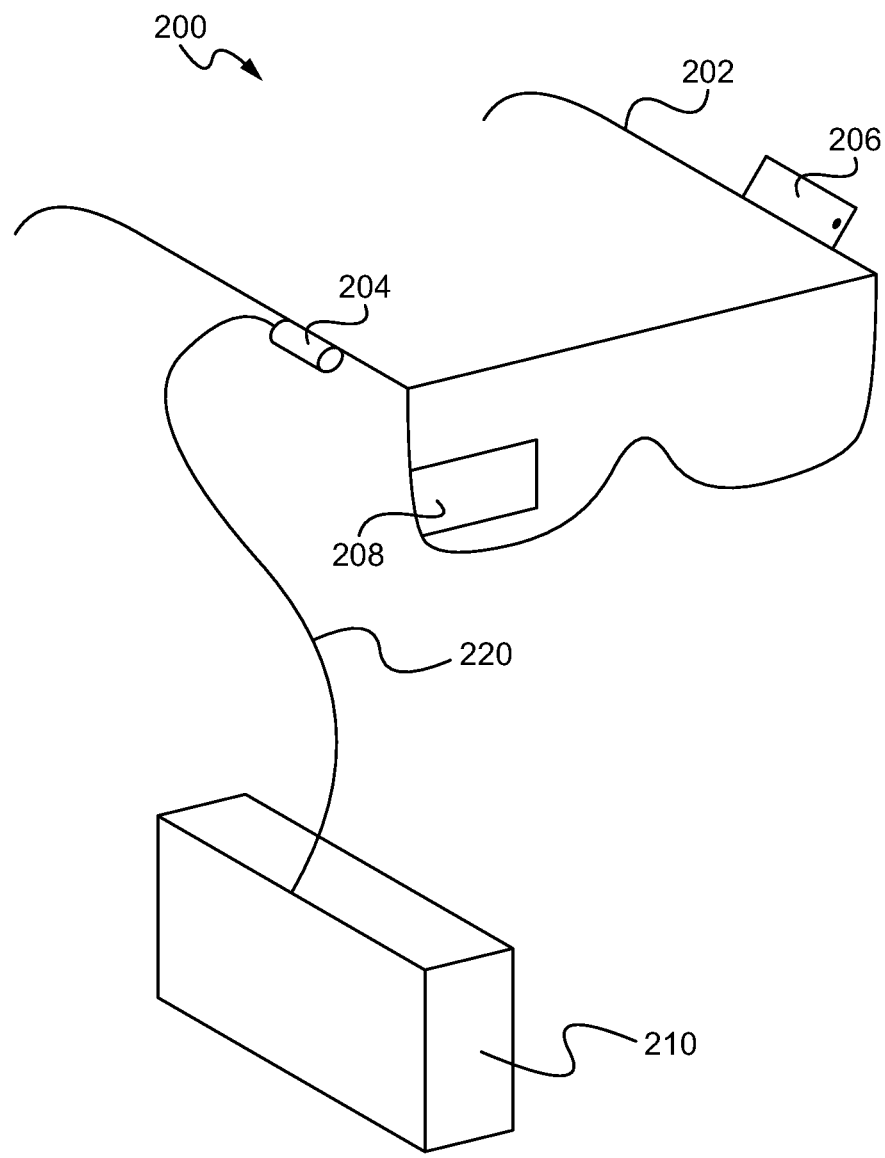
FIG. 3 illustrates a diagram of a wearable scribing system according to some embodiments.

FIG. 3 illustrates a view of the wearable scribing system 200 according to some embodiments. The wearable scribing system 200 includes glasses 202, a camera 204, a microphone 206, a display 208, a receiver/transmitter 210, and a tether/cable 220. The glasses 202 are able to be any shape, style and/or configuration. For example, the glasses 202 are able to have a single lens, multiple lenses or be goggles. A camera 204 and a microphone 206 are included with the glasses 202. In some embodiments, the camera 204 and the microphone 206 are detachable from the glasses 202, and in some embodiments the camera 204 and the microphone 206 are affixed to the glasses 202. The camera 204 and the microphone 206 are able to be positioned anywhere on the glasses 202 such as on the temples, the bridge, and/or the lens. In some embodiments, the camera 204 and the microphone 206 are a single component, and in some embodiments, they are separate components. A display 208 is also included anywhere on/in the glasses 202. For example, the display 208 is in front of part of one of the lenses of the glasses 202 so that a physician is able to easily view the display without being distracted from the non-display information in front of the physician. The tether 220 is able to be any type of wire or cable capable of communicating signals to/from the glasses 202 and the receiver/transmitter 210.

In some embodiments, the glasses 202 include wires within the glasses 202 to couple the receiver/transmitter 210 with the camera 204, the microphone 206 and the display 208. For example, the tether 220 couples with an internal wire which couples with the camera 204, the microphone 206 and the display 208.

The camera 204, the microphone 206 and the display 208 are able to communicate with the receiver/transmitter 210 via a tether 220 or wirelessly. For example, signals are sent to and from the camera 204, microphone 206, the display 208 and the receiver/transmitter 210 via the tether 220. In another example, the components have wireless capabilities and communicate using wireless transmissions.

The receiver/transmitter 210 is able to be any receiver/transmitter capable of receiving and transmitting information from/to devices such as the camera 204, the microphone 206 and the display 208. The receiver/transmitter 210 is also configured to receive and transmit information to a remote system (e.g., a computer be used by a scribe to electronically input information). In some embodiments, the receiver/transmitter 210 is configured to receive and transmit information to a cloud device which receives and transmits information to/from the remote system. The receiver/transmitter 210 is able to send information using wired or wireless communications. In some embodiments, the receiver/transmitter 210 encrypts information before sending information to the remote system so that only the intended recipient is able to access the information. In some embodiments, the receiver/transmitter 210 is a dedicated receiver/transmitter specifically designed for communicating with a scribe and wearable glasses with audio/video capabilities. In some embodiments, the receiver/transmitter 210 is a tablet computer, smart phone, smart watch, or another device.

The receiver/transmitter 210 is able to be configured to be worn on a user's belt with a clip, around their waist (e.g., in a waist pack), on their arm using an arm band, and/or any other location. In some embodiments, the receiver/transmitter 210 is not worn by the user.

In an exemplary implementation, a physician wears the glasses 202 for a patient consultation. The patient information is displayed on the display 208 for the physician to review while meeting with the patient. The conversation and the consultation with the patient is captured and recorded using the camera 204 and/or the microphone 206. The captured information is sent to the receiver/transmitter 210, and then the receiver/transmitter 210 sends the captured information to a remote system, where a scribe electronically inputs the information.

In some embodiments, the wearable scribing system 200 includes fewer or additional components. For example, in some embodiments, there is no tether, and the camera 204, microphone 206 and display 208 communicate wirelessly with the receiver/transmitter 210. As described above, in some embodiments, the wearable scribing system 200 is able to utilize Google Glass® or other augmented reality devices to communicate information to a scribe.

Figure 4:
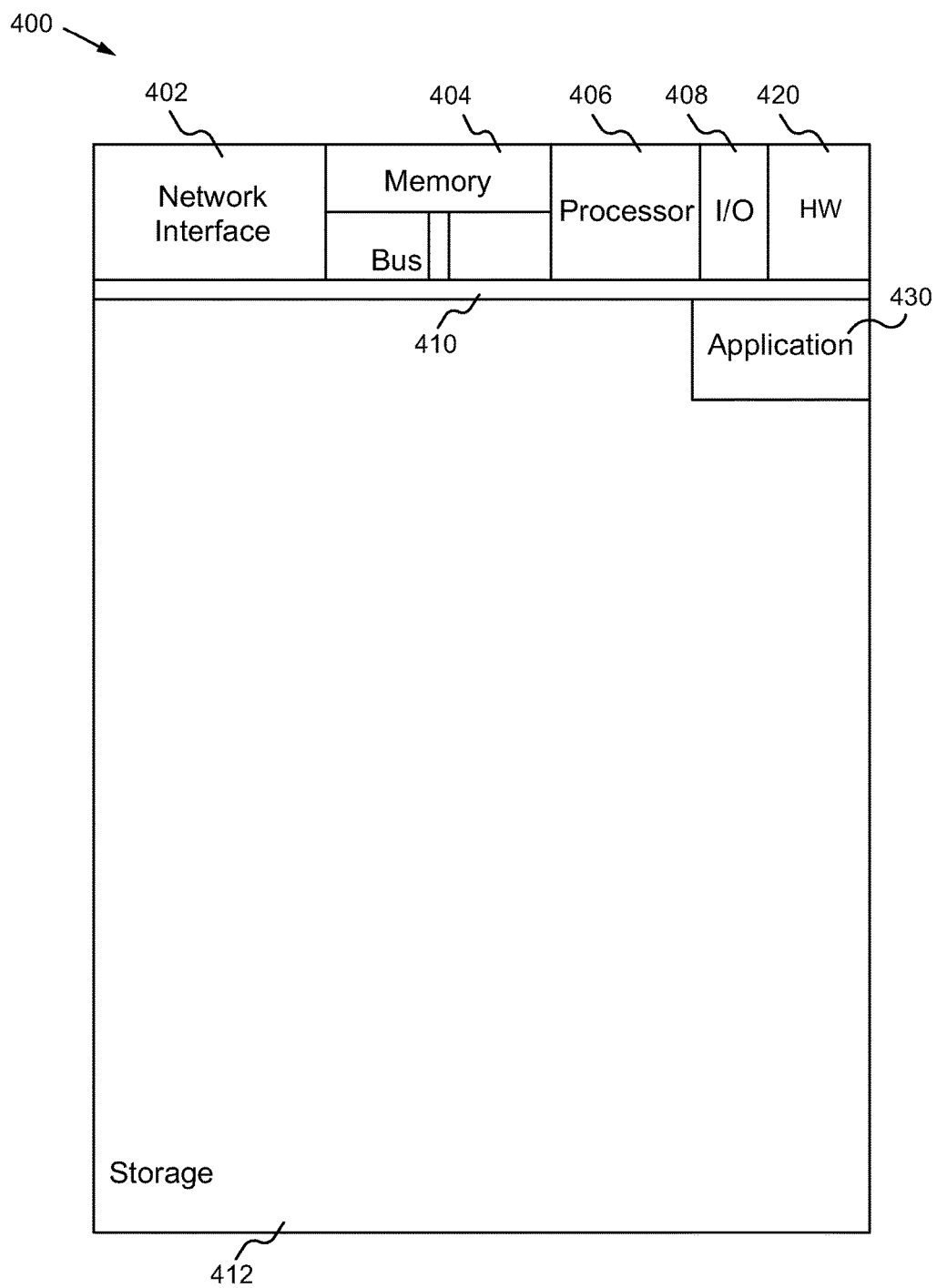
FIG. 4 illustrates a block diagram of an exemplary computing device configured to implement the wearable scribing system according to some embodiments.

FIG. 4 illustrates a block diagram of an exemplary computing device configured to implement the wearable scribing system according to some embodiments. The computing device 400 is able to be used to acquire, store, compute, process, communicate and/or display information such as audio, images, videos and text. For example, the computing device 400 is incorporated with glasses to capture/send/receive/display information. In another example, the computing device 400 is a receiver/transmitter. In another example, the computing device 400 is a desktop computer configured for receiving/sending information from/to a receiver/transmitter as well as receiving input by a scribe. The computing device 400 is able to perform any of the methods/steps described herein. In general, a hardware structure suitable for implementing the computing device 400 includes a network interface 402, a memory 404, a processor 406, I/O device(s) 408, a bus 410 and a storage device 412. The choice of processor is not critical as long as a suitable processor with sufficient speed is chosen. The memory 404 is able to be any conventional computer memory known in the art. The storage device 412 is able to include a hard drive, CDROM, CDRW, DVD, DVDRW, High Definition disc/drive, ultra-HD drive, flash memory card or any other storage device. The computing device 400 is able to include one or more network interfaces 402. An example of a network interface includes a network card connected to an Ethernet or other type of LAN. The I/O device(s) 408 are able to include one or more of the following: keyboard, mouse, monitor, screen, printer, modem, touchscreen, button interface and other devices. Wearable scribing system application(s) 430 used to perform the wearable scribing system methods are likely to be stored in the storage device 412 and memory 404 and processed as applications are typically processed. More or fewer components shown in FIG. 4 are able to be included in the computing device 400. In some embodiments, wearable scribing system hardware 420 is included. Although the computing device 400 in FIG. 4 includes applications 430 and hardware 420 for the wearable scribing system, the wearable scribing system is able to be implemented on a computing device in hardware, firmware, software or any combination thereof. For example, in some embodiments, the wearable scribing system applications 430 are programmed in a memory and executed using a processor. In another example, in some embodiments, the wearable scribing system hardware 420 is programmed hardware logic including gates specifically designed to implement the wearable scribing system.

In some embodiments, the wearable scribing system application(s) 430 include several applications and/or modules. In some embodiments, modules include one or more sub-modules as well. In some embodiments, fewer or additional modules are able to be included.

Examples of suitable computing devices include a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, high definition disc writer/player, ultra high definition disc writer/player), a television, an augmented reality device, a virtual reality device, a home entertainment system, smart jewelry (e.g., smart watch) or any other suitable computing device.

Figure 5:
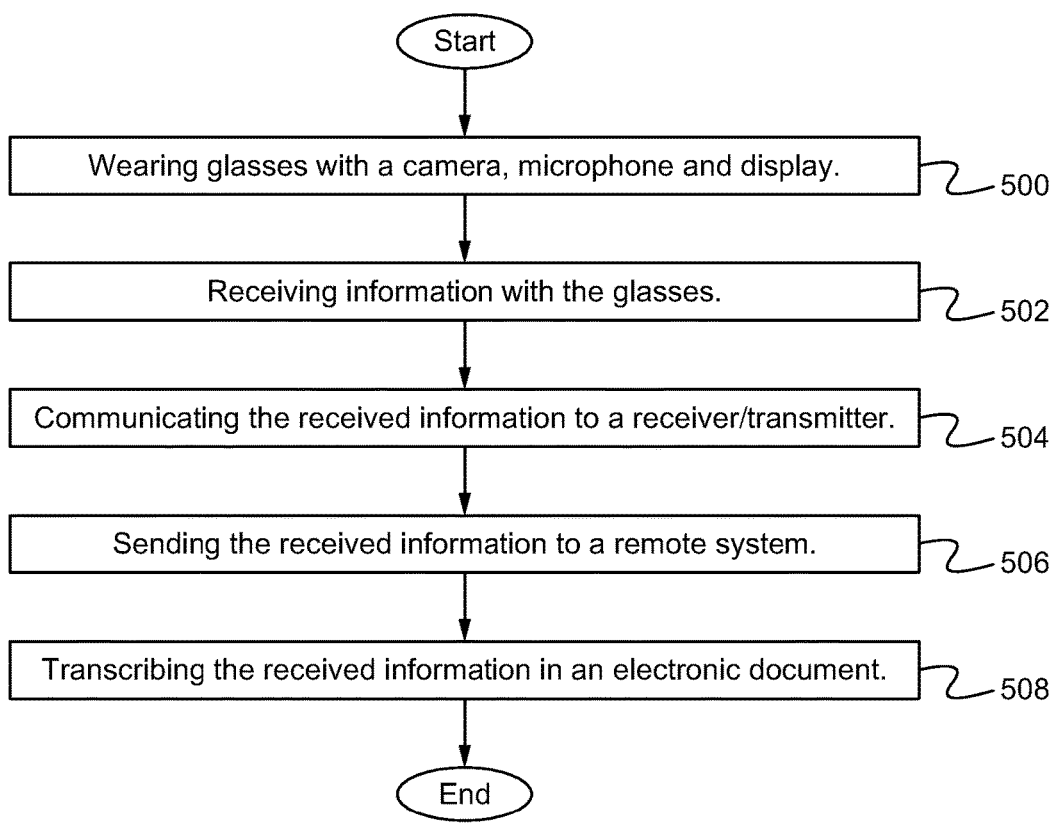
FIG. 5 illustrates a flowchart of a method of implementing the wearable scribing system according to some embodiments.

FIG. 5 illustrates a flowchart of a method of implementing the wearable scribing system according to some embodiments. In the step 500, a physician (or other user) wears the glasses with a camera, microphone and display and the receiver/transmitter. In some embodiments, there are one or more steps of initializing the glasses and the receiver/transmitter. For example, a button or the icon on the receiver/transmitter is pressed to turn on/link up the receiver/transmitter and the glasses. In the step 502, the glasses receive/capture information. For example, the camera of the glasses capture video, and the microphone captures audio (e.g., a patient describing a health concern to the physician). In the step 504, the glasses communicate the captured audio/video to the receiver/transmitter. In some embodiments, the receiver/transmitter includes a storage mechanism (e.g., internal memory) for storing the captured audio/video in case of transmission issues. In the step 506, the receiver/transmitter sends the audio/video to a remote location (e.g., to a computer and/or a scribe's headphones). In some embodiments, the receiver/transmitter sends the audio/video to a cloud device which sends the audio/video to the remote location. In the step 508, a user (e.g., scribe) transcribes what is in the audio/video into an electronic record. For example, the scribe types into a document or software application what the patient and/or physician say. In some embodiments, information goes back to the physician from the scribe such as video of the scribe at his computer via a webcam communicating with the receiver/transmitter which sends the video to the display of the glasses of the physician. In some embodiments, fewer or additional steps are implemented. In some embodiments, the order of the steps is modified.

Figure 6:
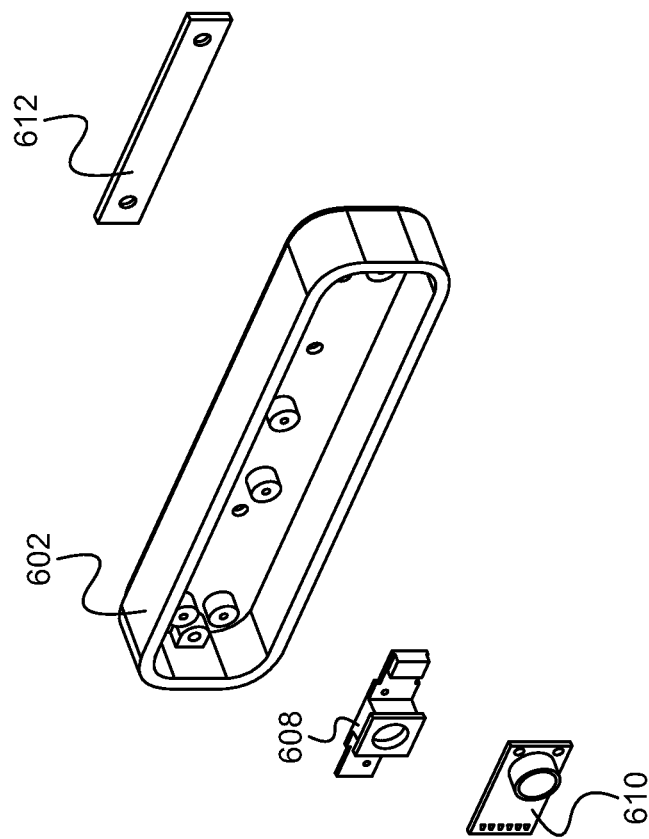
FIG. 6 illustrates a diagram of components of a wearable scribing system according to some embodiments.
Figure 6:
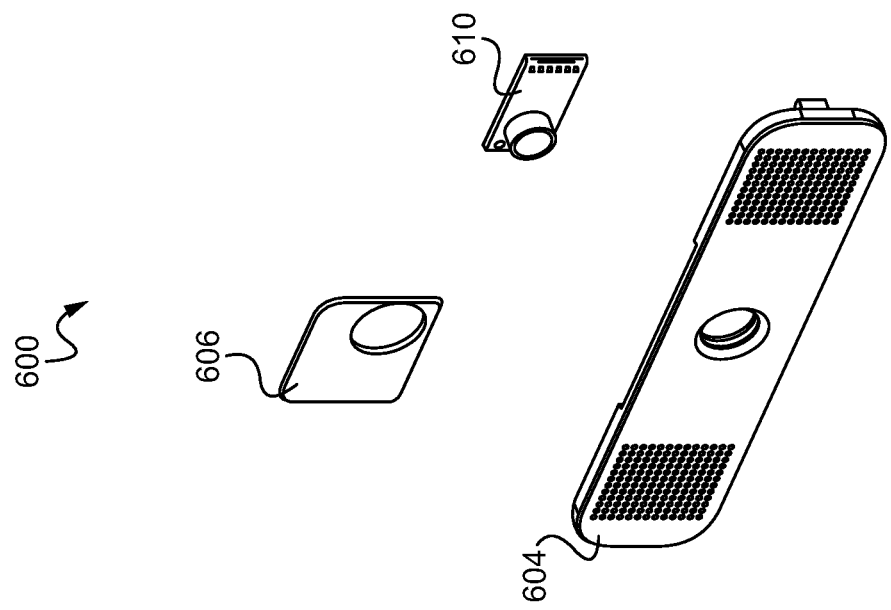

FIG. 6 illustrates a diagram of components of a wearable scribing system according to some embodiments. The wearable scribing system 600 includes a body 602, a face plate 604, a slidable camera cover 606 to cover a video camera 608, one or more microphones/speakers 610 and a back plate 612. The body 602 and face plate 604 are configured to hold/secure the slidable camera cover 606, video camera 608 and the one or more microphones/speakers 610. The body 602 is able to be any size, and in some embodiments, the body 602 is approximately 2-3 inches wide, 1 inch tall and less than 1 inch deep.

The face plate 604 includes an aperture for the video camera 608. The face plate 604 includes a plurality of small apertures to protect the microphones/speakers 610 but also increase the receptiveness of the microphones/speakers 610. The face plate 604 includes a recessed edge to enable the slidable camera cover 606 to fit between the face plate 604 and the body 602 and slide between a closed position and an open position.

The slidable camera cover 606 is able to be manually operated (e.g., using finger to move from one position to the other) or automatically operated (e.g., small motor moves the slidable camera cover 606 from one position to the other). In some embodiments, the slidable camera cover 606 is lockable in the closed position or the open position. In some embodiments, moving the slidable camera cover 606 into the open position turns the video camera 608 and/or the wearable scribing system 600 on, and moving the slidable camera cover 606 into the closed position turns the video camera 608 and/or the wearable scribing system 600 off In some embodiments, the microphones/speakers 610 of the wearable scribing system 600 are able to be on while the video camera 608 is covered by the slidable camera cover 606. In some embodiments, a camera cover is implemented in another manner (e.g., not slidable).

In some embodiments, additional circuitry is included such as a processor, memory, networking/wireless capabilities, and/or any other circuitry to operate the wearable scribing system 600. In some embodiments, voice-operation capabilities are implemented. For example, a user is able to turn on/off/mute the video camera 608 and/or the microphones/speakers 610 using voice commands.

The video camera 608 is able to be any video camera. In some embodiments, the video camera 608 is a wide angle camera. In some embodiments, the video camera 608 is able to take videos and capture images. For example, the user is able to give a voice command or press a button to take a picture. In some embodiments, the video camera 608 automatically turns on and/or records when the slidable camera cover 606 is in the open position. In some embodiments, a button or voice-command causes the video camera 608 to turn on and/or start recording.

The microphones/speakers 610 are able to be any microphone and/or speaker combination. For example, there may be one microphone and no speakers; two microphones and no speakers; one microphone and one speaker; or two speakers and no microphone. Any number of microphones and/or speakers are able to be implemented. In some embodiments, the microphone is a high sensitivity microphone. The microphones/speakers 610 are able to be turned on in any manner (e.g., automatically when the slidable camera cover 606 is open, using a button or via voice-command) The speakers 610 are able to be used for any manner such as to project a scribe's voice.

In some embodiments, the back plate 612 is magnetic, adhesive (e.g., stickable), and/or includes a coupling mechanism (e.g., a clip, pin) to secure the wearable scribing system 600 to clothing or another object. The wearable scribing system 600 is able to be worn in any manner such as on a user's torso.

In some embodiments, the wearable scribing system 600 includes a port and the accompanying hardware (e.g., wire/cable) for communicating data with a mobile device (e.g., smart phone). In some embodiments, the wearable scribing system 600 includes a wireless communication implementation (e.g., Bluetooth®) to communicate with the mobile device. The mobile device then communicates with a scribe's device using cellular and/or Wi-Fi. In some embodiments, the wearable scribing system 600 includes networking capabilities (e.g., cellular and/or Wi-Fi) to communicate directly with a scribe's device. In some embodiments, the wearable scribing system 600 includes a display to display any information. For example, text, images, and/or videos are able to be displayed using the display. The display is able to be located anywhere on the wearable scribing system, for example, on the front, back, top, bottom or sides. In some embodiments, the wearable scribing system is able to couple to an external display.

Figure 7:
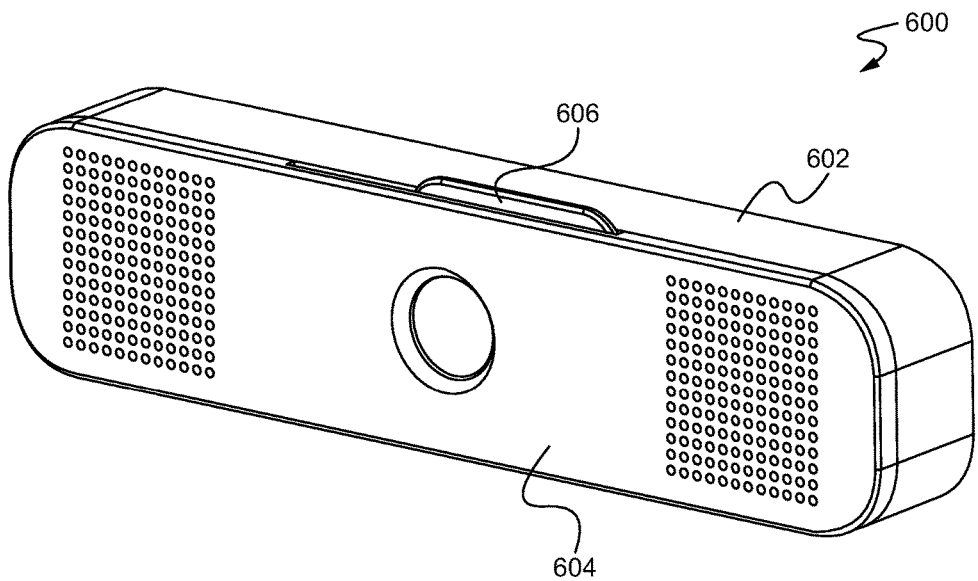
FIG. 7 illustrates a view of the wearable scribing system with a camera cover in the closed position according to some embodiments.

FIG. 7 illustrates a view of the wearable scribing system with a camera cover in the closed position according to some embodiments. As shown, the slidable camera cover 606 is in the closed position such that the video camera is covered. The slidable camera cover 606 is able to be shaped in any manner that is capable of covering the video camera. The slidable camera cover 606 includes a tab that is able to be moved using a user's finger to slide the slidable camera cover 606 between the open and closed positions. By sliding the slidable camera cover 606 in the closed position, a patient is ensured that the video camera is not currently capturing video.

Figure 8:
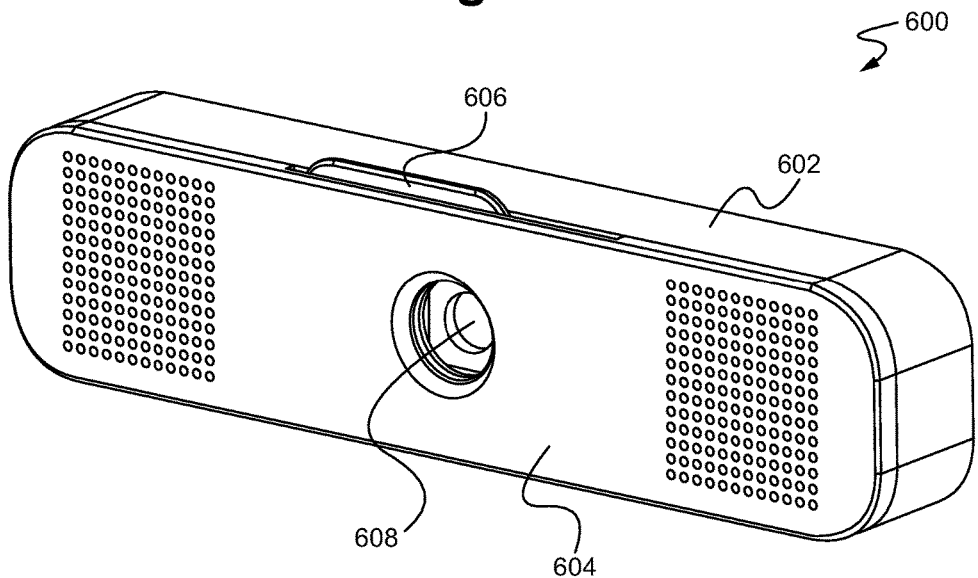
FIG. 8 illustrates a view of the wearable scribing system with a camera cover in the open position according to some embodiments.

FIG. 8 illustrates a view of the wearable scribing system with a camera cover in the open position according to some embodiments. By sliding the slidable camera cover 606 to the open position, the video camera (in particular, the lens of the video camera) is exposed so that the video camera is able to acquire video.

Figure 9:
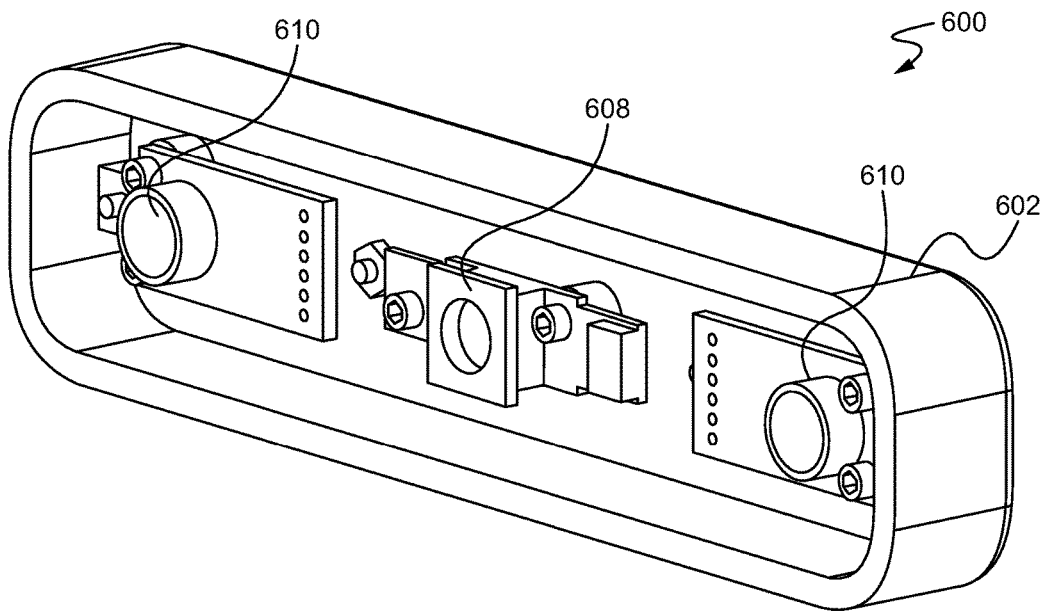
FIG. 9 illustrates a cross-sectional view of the wearable scribing system according to some embodiments.

FIG. 9 illustrates a cross-sectional view of the wearable scribing system according to some embodiments. The cross-sectional view shows the video camera 608 and the microphones/speakers 610 positioned within the body 602. Any orientation/configuration of the video camera 608 and the microphones/speakers 610 is possible. For example, the video camera 608 and/or the microphones/speakers 610 are positioned outside of the body 602.

Figure 10:
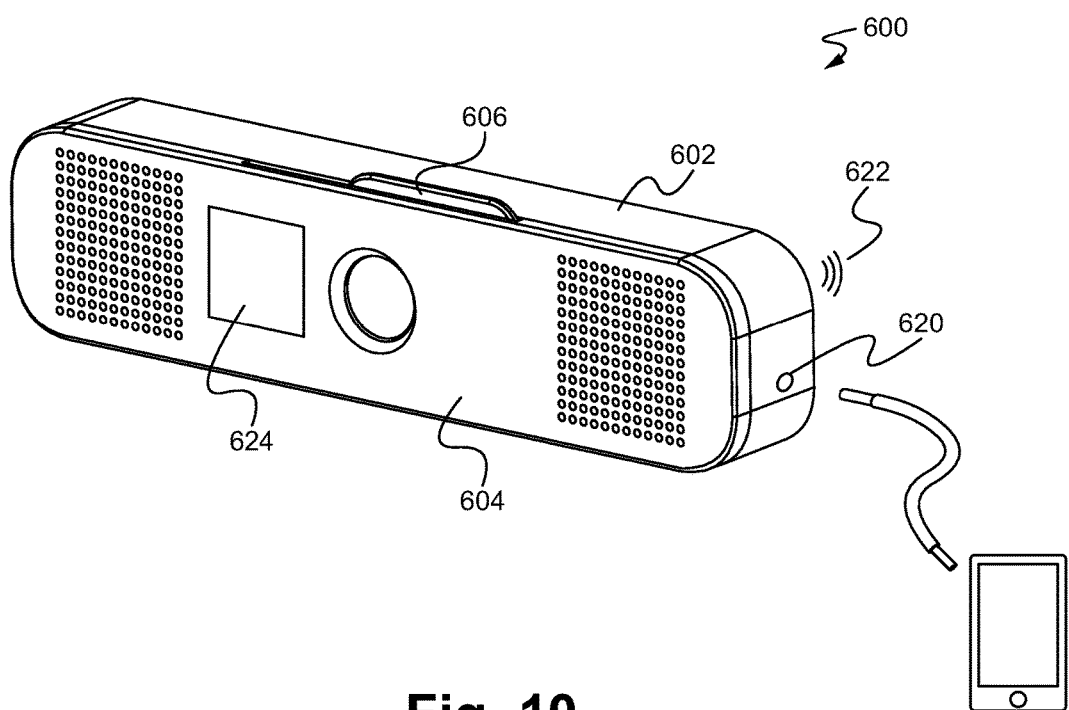
FIG. 10 illustrates a view of the wearable scribing system and a mobile device according to some embodiments.

FIG. 10 illustrates a view of the wearable scribing system and a mobile device according to some embodiments. In some embodiments, the wearable scribing system 600 includes a port 620 and the accompanying hardware (wire/cable) for communicating data with a mobile device (e.g., smart phone). In some embodiments, the wearable scribing system 600 includes a wireless communication implementation (e.g., Bluetooth®) 622 to communicate with the mobile device. The mobile device then communicates with a scribe's device using cellular, Wi-Fi and/or another network, as described herein. In some embodiments, the wearable scribing system 600 includes networking capabilities (e.g., cellular and/or Wi-Fi) to communicate directly with a scribe's device. In some embodiments, the wearable scribing system 600 includes a display 624 to display any information. For example, text, images, and/or videos are able to be displayed using the display 624. The display 624 is able to be located anywhere on the wearable scribing system 600, for example, on the front, back, top, bottom or sides. In some embodiments, the wearable scribing system 600 is able to couple to an external display.

In some embodiments, the wearable scribing system 600 includes additional components for operation such as buttons, tabs, switches to turn on/off components such as the video camera 608, the microphones/speakers 610 and/or the display 624. In some embodiments, LEDs or other visual indicators are included to alert a user and/or patient that one or more components are on or off. For example, an LED lights up red to indicate that the microphone has been turned off, or an LED lights up greed to indicate the microphone is on.

Figure 11:
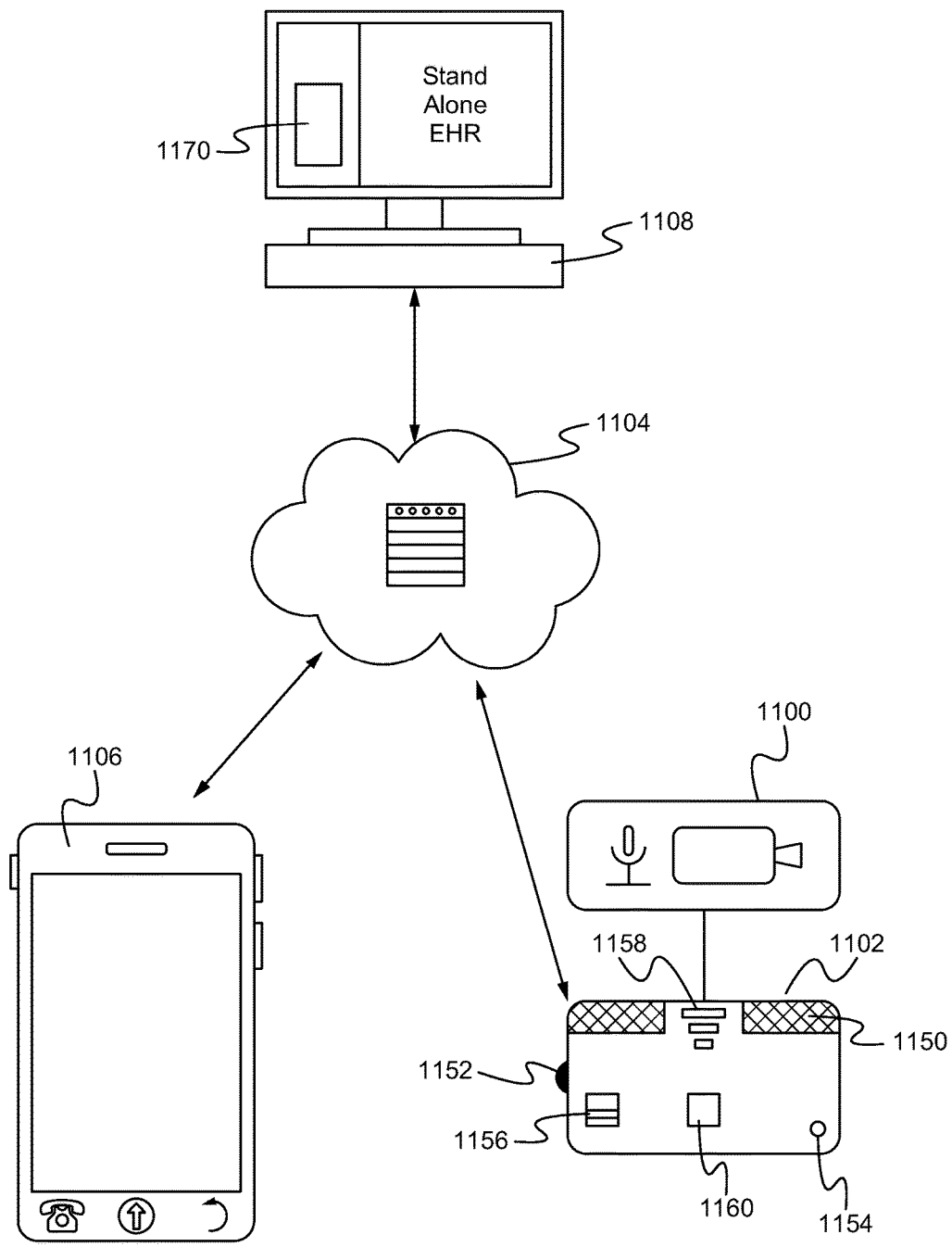
FIG. 11 illustrates a view of the wearable scribing system and a mobile device according to some embodiments.

FIG. 11 illustrates a view of the wearable scribing system and a mobile device according to some embodiments. A communication unit includes a recording device 1100 and a processor component 1102. The recording device 1100 includes a video camera and a microphone to record video or sound. The processor component 1102 includes speakers 1150 (to hear audio received from a scribe), a volume control 1152 for the speakers, a headphone jack 1154 to enable the physician to use headphones to listen to the scribe instead of with the speakers, an on/off switch 1156, a battery level indicator 1158 for a rechargeable/replaceable battery, and/or circuitry 1160 (e.g., a processor, storage). The processor component 1102 is able to include fewer or additional components. A physician wears the recording device 1100 anywhere (e.g., on the upper torso). The recording device 1100 is linked to the processor component 1102 which resides anywhere (e.g., in the pocket of the physician or on a belt clip). The recording device 1100 and the processor component 1102 are coupled wirelessly (e.g., Bluetooth®) or via a hard wire. The recording device 1100 is able to include a lens cover that is able to be placed when desired as an added safety measure to ensure no transmission of video, as described herein.

The processor component 1102 compresses and formats the video and audio received from the video camera and microphone components and transmits (e.g., via Wi-Fi) the compressed, formatted data to a server 1104 (e.g., in the cloud) which then sends the data to a remote device such as a mobile device 1106 (e.g., smart phone) or a scribe computer 1108. The processor component 1102 compresses and formats the video and audio input in any manner such as by implementing compression and formatting software which receives raw video/audio data and compresses and formats the data appropriately.

The server 1104 coordinates the interfaces and interactions between the processor component 1102, the mobile device 1106 and the scribe computer 1108. For example, the server 1104 is configured to determine which data goes to which device, which data is encrypted or further encrypted, and so on. Furthering the example, the server 1104 determines which scribe computer 1108 is available to receive the compressed, formatted data by receiving or accessing an availability flag of the scribe computers.

The mobile device 1106 (e.g., physician's smart phone) is able to be an Android or iOS device (or other device). The mobile device 1106 couples via WiFi (or other wireless protocol) to the server 1104. Prior to coupling with the server 1104, the mobile device 1106 syncs to the processor component 1102 with a brief hard wire connection. For example, the mobile device 1106 couples with the processor component 1102 using a cable, and a signal or other verification implementation is used to determine that the mobile device 1106 is secure and gains access to the server 1104 such as by providing a cookie or other verification/validation unit to the mobile device 1106 which is checked by the server 1104 which indicates the mobile device 1106 has been verified, and if a mobile device does not meet the verification/authentication requirement (e.g., does not have the appropriate credentials), then access to the server 1104 or other devices is denied. The hard wire connection adds a layer of security and prevents remote access of any physician communication unit or processor component. The mobile device 1106 is able to perform the following: start and end the communication unit connection to the scribe computer 1108, turn on and off the communication until video or audio to the scribe, turn on and off the communication until audio from the scribe, display the camera output from the communication unit which enables the physician to directly see the same video feed the scribe is seeing, and allow for secure instant messaging between the physician and the scribe or the physician to other physicians.

The scribe computer 1108 performs the following: receives audio and video input from the physician which allows the scribe to view and hear the physician—patient interaction, enable the scribe to speak with the physician via a desktop microphone, mute/turn off audio from the physician, communicate via instant messaging with the mobile device 1106, and input notes based on the audio/video received. The physician documents an interaction with a patient in real time in a separately running electronic health record. The scribe computer 1108 displays the communication unit video. In some embodiments, the scribe computer 1108 displays the communication unit video and other content in a split screen format.

The wearable scribing system of FIG. 11 is able to include any of the features/components described herein.

By providing more features on the processing component 1102 and not utilizing an operating system similar to Android OS on the processing component 1102, any changes made by operating system companies such as changes to the Android OS will not affect the operation of the processing component 1102. Additionally, by having a separate battery for the processing component 1102, the time frame that remote scribe services are able to be utilized prior to the need for recharging the hardware is increased. Thus, the battery capacity of the mobile phone is no longer a restriction. Furthermore, having a separate processing component 1102 in the physician communication unit improves the reliability of transmission between physician and scribe. Without the processing component 1102, if the mobile phone was running other applications requiring strong processing power simultaneous to ScribeLink, functionality of the software would suffer. Additional independence from a mobile device (e.g., smart phone) by utilizing a separate processing component provides many benefits.

Figure 12:
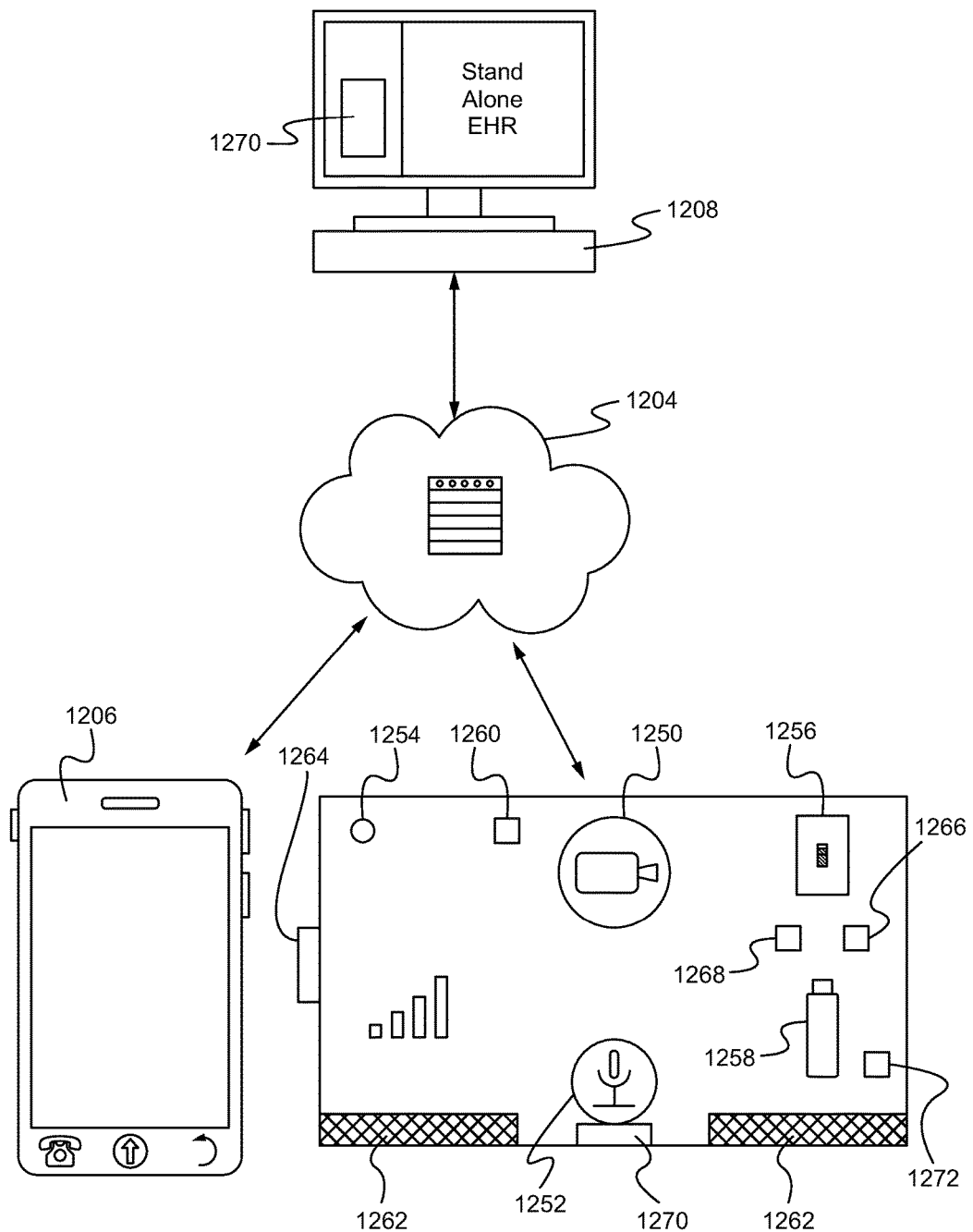
FIG. 12 illustrates a view of a single unit wearable scribing system and a mobile device according to some embodiments.

FIG. 12 illustrates a view of a single unit wearable scribing system and a mobile device according to some embodiments. A single unit wearable scribing system 1200 is a single unit (e.g., in the same casing/enclosure) including recording components and processing components. The single unit wearable scribing system 1200 includes a video camera 1250 and/or a microphone 1252 to record video or sound. The single unit wearable scribing system 1200 includes a headphone jack 1254 to enable the physician to use headphones to listen to the scribe instead of with the speakers, an on/off switch 1256, a battery level indicator 1258 for a rechargeable/replaceable battery, circuitry 1260 (e.g., a processor, storage for applications such as compression and communication applications, wife components/capabilities), speakers 1262 (to hear audio received from a scribe), a volume control 1264 for the speakers 1262 and a USB connector 1270. The single unit wearable scribing system 1200 is able to include any type of power source such as a permanent battery 1266 (e.g., 5 minute backup) and/or a removable/rechargeable battery 1268. In some embodiments, the single unit wearable scribing system 1200 includes a noise canceling mechanism (implemented in software, hardware or a combination thereof). The single unit wearable scribing system 1200 is able to include fewer or additional components. The video camera 1250 is able to include a lens cover that is able to be placed when desired as an added safety measure to ensure no transmission of video, as described herein. A physician wears the single unit wearable scribing system 1200 anywhere (e.g., on the upper torso).

The circuitry 1260 (e.g., processor and more) compresses and formats the video and audio received from the video camera 1250 and/or microphone 1252 and transmits (e.g., via Wi-Fi) the compressed, formatted data to a server 1204 (e.g., in the cloud) which then sends the data to a remote device such as a mobile device 1206 (e.g., smart phone) or a scribe computer 1208. The circuitry 1260 compresses and formats the video and audio input in any manner such as by implementing compression and formatting software which receives raw video/audio data and compresses and formats the data appropriately.

The server 1204 coordinates the interfaces and interactions between the single unit wearable scribing system 1200, the mobile device 1206 and the scribe computer 1208. For example, the server 1204 is configured to determine which data goes to which device, which data is encrypted or further encrypted, and so on. Furthering the example, the server 1204 determines which scribe computer 1208 is available to receive the compressed, formatted data by receiving or accessing an availability flag of the scribe computers.

The mobile device 1206 (e.g., physician's smart phone) is able to be an Android or iOS device (or other device). The mobile device 1206 couples via WiFi (or other wireless protocol) to the server 1204. Prior to coupling with the server 1204, the mobile device 1206 syncs to the single unit wearable scribing system 1200 with a brief hard wire connection. For example, the mobile device 1206 couples with the single unit wearable scribing system 1200 using a cable, and a signal or other verification implementation is used to determine that the mobile device 1206 is secure and gains access to the server 1204 such as by providing a cookie or other verification/validation unit to the mobile device 1206 which is checked by the server 1204 which indicates the mobile device 1206 has been verified, and if a mobile device does not meet the verification/authentication requirement (e.g., does not have the appropriate credentials), then access to the server 1204 or other devices is denied. The hard wire connection adds a layer of security and prevents remote access of any physician communication unit or processor component. The mobile device 1206 is able to perform the following: start and end the communication unit connection to the scribe computer 1208, turn on and off the communication until video or audio to the scribe, turn on and off the communication until audio from the scribe, display the camera output from the communication unit which enables the physician to directly see the same video feed the scribe is seeing, and allow for secure instant messaging between the physician and the scribe or the physician to other physicians.

The scribe computer 1208 performs the following: receives audio and video input from the physician which allows the scribe to view and hear the physician—patient interaction, enable the scribe to speak with the physician via a desktop microphone, mute/turn off audio from the physician, communicate via instant messaging with the mobile device 1206, and input notes based on the audio/video received. The physician documents an interaction with a patient in real time in a separately running electronic health record. The scribe computer 1208 displays the communication unit video. In some embodiments, the scribe computer 1208 displays the communication unit video and other content in a split screen format.

In some embodiments, the single unit wearable scribing system 1200 (or any other device described herein such as the processor component 1102) is able to have direct Wi-Fi connectivity (e.g., by having its own subscriber identity module (SIM) card 1272). The direct Wi-Fi connectivity enables the single unit wearable scribing system 1200 to access a cellular network (or other network) and then wirelessly share the data connection with other devices such as the mobile device 1206. In some embodiments, the direct Wi-Fi connectivity is utilized to enable secure communications between specified devices (e.g., the mobile device 1206 and the scribe computer 1208 through the single unit wearable scribing system 1200).

The wearable scribing system of FIG. 12 is able to include any of the features/components described herein.

By providing more features on the single unit wearable scribing system and not utilizing an operating system similar to Android OS on the single unit wearable scribing system, any changes made by operating system companies such as changes to the Android OS will not affect the operation of the single unit wearable scribing system. Additionally, by having a separate battery for the single unit wearable scribing system, the time frame that remote scribe services are able to be utilized prior to the need for recharging the hardware is increased. Thus, the battery capacity of the mobile phone is no longer a restriction. Furthermore, having a separate single unit wearable scribing system improves the reliability of transmission between physician and scribe. Without the single unit wearable scribing system, if the mobile phone was running other applications requiring strong processing power simultaneous to ScribeLink, functionality of the software would suffer. Additional independence from a mobile device (e.g., smart phone) by utilizing a separate single unit wearable scribing system provides many benefits.

In some embodiments, the mobile device 1206 is configured to enable secure communications. For example, a user is able to switch to a second screen from within the same software/application to communicate with the scribe (e.g., scribelink). From the second screen, the user is able to securely (e.g., HIPAA compliant): capture photos and videos, send and receive photos and videos, send and receive text messages, have a chat (e.g., video chat) session. The chat session is able to include secure instant messaging. In some embodiments, the chat session utilizes information acquired using the single unit wearable scribing system. For example, the information acquired using the single unit wearable scribing system is able to be transmitted using secure instant messaging (or another secure communication). Physicians, nurses, scribes, patients and others are able to utilize the secure applications (e.g., chat/instant messaging) with the mobile device. Instant messaging is able to include sending data (e.g., text, video, audio) from one device to another such that the data appears on the receiving device nearly instantaneously.

Figure 13:
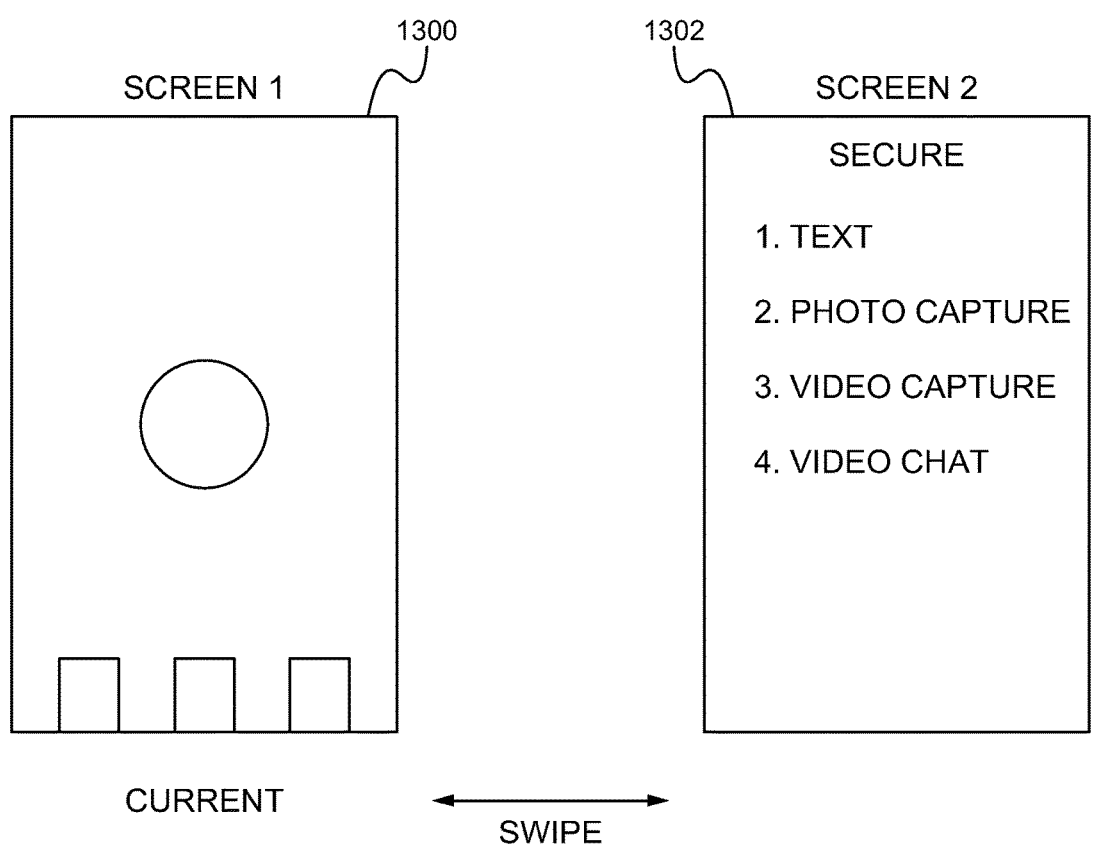
FIG. 13 illustrates a diagram of a secure communication application within the physician mobile device according to some embodiments.

FIG. 13 illustrates a diagram of a secure communication application within the physician mobile device according to some embodiments. A user (e.g., physician) is able to access a secure communication application using a device (e.g., a smart phone, a personal computer, a single unit wearable system). The user is able to access the secure communication application in any manner such as by swiping to the secure communication application. For example, the user is able to swipe from a first screen 1300 to a second screen 1302, where the second screen 1302 provides communication options. The secure application enables a user to acquire content (e.g., photos, videos, audio), send or receive content, send and receive text, and/or have video chats/conferences. In some embodiments, the content to be sent/received is received from the single unit wearable scribing system. In some embodiments, a similar configuration exists for the scribe on their computer, such that the scribe is able to access a secure communication application. The scribe also will have the capability, in a secure manner, to send and/or receive content, send and/or receive text, and/or have video chats/conferences.

To utilize the wearable scribing system, a physician wears the wearable scribing system (e.g., on his torso) for any type of procedure or patient meeting. The video camera and the microphone of the wearable scribing system automatically acquire data and transmit the data to a mobile device which transmits the data to a remote system where a scribe inputs the information into an electronic document.

In operation, the wearable scribing system enables the physician to focus on the patient, rather than a computer running an EHR. The wearable scribing system permits doctors to function as doctors and not data entry specialists. By not having to write, type, or dictate, physician efficiency and job satisfaction will vastly improve. The wearable scribing system lets the scribe code the patient encounter for billing in a quicker and more thorough manner than current methods.

Although the wearable scribing system has been described relative to physicians, any user is able to utilize the wearable scribing system such as a police officer, an attorney, government employee and others.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. An apparatus comprising:
   a. a body;
   b. a recording device;
   c. a processor contained within the body configured to process one or more compression and formatting applications to compress and format data received from the recording device into compressed, formatted data; and
   d. a communication mechanism configured for sending the compressed, formatted data to an external device, wherein the external device is used to input an electronic document, wherein the body, the recording device, the processor and the communication mechanism are contained in a single unit, wherein the communication mechanism is configured for sending the compressed, formatted data to a cloud-based server device, and the cloud-based server device is configured to determine which compressed, formatted data goes to which scribe computing device by determining which scribe computing device is available by receiving or accessing an availability flag of the scribe computing device.

2. The apparatus of claim 1 wherein the apparatus is wearable.

3. The apparatus of claim 1 wherein the apparatus is wearable on a user's torso.

4. The apparatus of claim 1 wherein the cloud-based server device is configured for sending the compressed, formatted data to the external device.

5. The apparatus of claim 1 wherein the apparatus communicates with a mobile device.

6. The apparatus of claim 1 wherein the apparatus is coupled with a mobile device via a hard wire connection to provide the mobile device with access to a server device.

7. A method comprising:
   a. acquiring audio and video with a single wearable unit secured on a user;
   b. compressing and formatting the audio and video with the single wearable unit into a compressed, formatted data;
   c. sending the compressed, formatted data to a cloud-based server device; and
   d. sending the compressed, formatted data to an external device, wherein the external device is used to input an electronic document, wherein the cloud-based server device is configured to determine which compressed, formatted data goes to which external device by determining which external device is available by receiving or accessing an availability flag of the external device.

8. The method of claim 7 wherein the cloud-based server device is configured for sending the compressed, formatted data to the external device.

9. The method of claim 7 further comprising communicating with a mobile device with the single wearable unit.

10. The method of claim 9 further comprising accessing a secured communication system within an application for communicating with the external device.

11. The method of claim 10 wherein the secured communication system enables: capturing photographs and videos, sending and receiving the photographs and videos, sending and receiving messages, or participating in a video chat.

12. A system comprising:
   a. an external device;
   b. a cloud-based server device configured for communicating with the external device; and
   c. a single wearable unit configured for capturing audio and video and compressing and formatting the audio and video into compressed, formatted data and sending the compressed, formatted data to the cloud-based server device which sends the compressed, formatted data to the external device, wherein the cloud-based server device is configured to determine which compressed, formatted data goes to which external device by determining which external device is available by receiving or accessing an availability flag of the external device.

13. The system of claim 12 wherein the single wearable unit is wearable on a user's torso.

14. The system of claim 12 wherein the single wearable unit includes a video camera and a microphone.

15. The system of claim 14 wherein the video camera further comprises a slidable cover, wherein the slidable cover is configured to slide between an open position and a closed position to cover the video camera.

16. The system of claim 12 further comprising a mobile device which couples to the single wearable unit using a hard wire to be authenticated before gaining access to the cloud-based server device.

17. The system of claim 12 wherein the single wearable unit communicates with the cloud-based server device using Wi-Fi, a cellular network and/or the Internet.

18. The system of claim 12 wherein the single wearable unit includes speakers, a volume control for the speakers, and a headphone jack.

19. The system of claim 12 further comprising a mobile device configured for accessing a secured communication system within an application for communicating with the external device.

20. The system of claim 19 wherein the secured communication system enables: capturing photographs and videos, sending and receiving the photographs and videos, sending and receiving messages, or participating in a video chat.

* * * * *